(12) United States Patent
Stockton, X et al.

(10) Patent No.: US 10,848,848 B2
(45) Date of Patent: *Nov. 24, 2020

(54) EARPHONES FOR MEASURING AND ENTRAINING RESPIRATION

(71) Applicant: Bose Corporation, Framingham, MA (US)

(72) Inventors: Andrew Jackson Stockton, X, Miami, FL (US); Andrew D. Dominijanni, Newton, MA (US); Daniel M. Gauger, Jr., Berlin, MA (US); Harsh Anilkant Mankodi, Brighton, MA (US)

(73) Assignee: Bose Corporation, Framingham, MA (US)

( * ) Notice: Subject to any disclaimer, the term of this patent is extended or adjusted under 35 U.S.C. 154(b) by 190 days.

This patent is subject to a terminal disclaimer.

(21) Appl. No.: 15/655,857

(22) Filed: Jul. 20, 2017

(65) Prior Publication Data

US 2019/0028789 A1    Jan. 24, 2019

(51) Int. Cl.
*H04R 1/10* (2006.01)
*A61M 21/02* (2006.01)
(Continued)

(52) U.S. Cl.
CPC ....... *H04R 1/1016* (2013.01); *A61B 5/02438* (2013.01); *A61B 5/0816* (2013.01);
(Continued)

(58) Field of Classification Search
CPC . H04R 1/1016; A61B 5/02438; A61B 5/0816; A61B 5/4815; A61M 21/02
See application file for complete search history.

(56) References Cited

U.S. PATENT DOCUMENTS

| | | | |
|---|---|---|---|
| 5,143,078 A | 9/1992 | Mather et al. | |
| 7,850,619 B2 * | 12/2010 | Gavish | A61B 7/003 600/484 |

(Continued)

FOREIGN PATENT DOCUMENTS

| | | |
|---|---|---|
| GB | 2532745 A | 6/2016 |
| WO | 2010054863 A1 | 5/2010 |

(Continued)

OTHER PUBLICATIONS

International Search Report and Written Opinion dated Oct. 10, 2018 for International application No. PCT/US2018/043058.

(Continued)

*Primary Examiner* — Sunita Joshi
(74) *Attorney, Agent, or Firm* — Bose Corporation

(57) ABSTRACT

An earphone includes a loudspeaker, a microphone, a housing supporting the loudspeaker and microphone, and an ear tip surrounding the housing and configured to acoustically couple both the loudspeaker and the microphone to an ear canal of a user, and to acoustically close the entrance to the user's ear canal. A processor provides output audio signals to the loudspeaker which represent sounds across a first frequency band, the audio signals including a notch in which the sounds lack energy within a second frequency band narrower than the first frequency band, receives input audio signals from the microphone, applies a band-pass filter to the input audio signals to limit the input audio signals to a third frequency band contained within the second frequency band, and demodulates the filtered input audio signals to compute a rate of respiration corresponding to energy in the input audio signals in the third frequency band.

14 Claims, 6 Drawing Sheets

(51) Int. Cl.
- *A61B 7/00* (2006.01)
- *H04R 1/22* (2006.01)
- *A61M 21/00* (2006.01)
- *H04R 3/02* (2006.01)
- *A61B 5/024* (2006.01)
- *A61B 5/08* (2006.01)
- *A61B 5/00* (2006.01)

(52) U.S. Cl.
CPC ............ *A61B 5/6817* (2013.01); *A61B 7/003* (2013.01); *A61M 21/02* (2013.01); *H04R 1/1058* (2013.01); *H04R 1/22* (2013.01); *A61B 5/6803* (2013.01); *A61B 2562/0204* (2013.01); *A61M 2021/0027* (2013.01); *A61M 2021/0088* (2013.01); *A61M 2205/3375* (2013.01); *A61M 2230/42* (2013.01); *H04R 1/1083* (2013.01); *H04R 3/02* (2013.01)

(56) References Cited

U.S. PATENT DOCUMENTS

| | | | |
|---|---|---|---|
| 9,635,452 B2 * | 4/2017 | Cheng | H04R 1/1016 |
| 2002/0091049 A1 | 7/2002 | Hisano et al. | |
| 2004/0077934 A1 | 4/2004 | Massad | |
| 2007/0118011 A1 | 5/2007 | Harrison et al. | |
| 2008/0146890 A1 | 6/2008 | LeBoeuf et al. | |
| 2008/0171945 A1 | 7/2008 | Dotter | |
| 2009/0143636 A1 | 6/2009 | Mullen et al. | |
| 2010/0125218 A1 | 5/2010 | Haartsen et al. | |
| 2010/0240945 A1 | 9/2010 | Bikko | |
| 2011/0295083 A1 | 12/2011 | Doelling et al. | |
| 2012/0156933 A1 * | 6/2012 | Kreger | A61B 5/0245 439/625 |
| 2012/0203077 A1 | 8/2012 | He et al. | |
| 2012/0225412 A1 | 9/2012 | Wagner | |
| 2012/0256933 A1 | 10/2012 | Airey et al. | |
| 2013/0034258 A1 | 2/2013 | Lin | |
| 2013/0090567 A1 * | 4/2013 | Lee | A61B 7/04 600/529 |
| 2014/0141395 A1 | 5/2014 | Gavish et al. | |
| 2015/0150515 A1 | 6/2015 | Strachan | |
| 2015/0258301 A1 * | 9/2015 | Trivedi | G06F 16/636 600/28 |
| 2015/0351688 A1 | 12/2015 | Just et al. | |
| 2016/0151603 A1 * | 6/2016 | Shouldice | A61B 5/486 600/28 |
| 2017/0325718 A1 | 11/2017 | Boesen et al. | |
| 2017/0347177 A1 | 11/2017 | Masaki et al. | |
| 2017/0367658 A1 | 12/2017 | LeBoeuf et al. | |
| 2018/0338193 A1 | 11/2018 | Wallace et al. | |
| 2019/0022349 A1 | 1/2019 | Kirszenblat et al. | |
| 2019/0028789 A1 | 1/2019 | Stockton et al. | |

FOREIGN PATENT DOCUMENTS

| | | |
|---|---|---|
| WO | 2017011431 A2 | 1/2017 |
| WO | 2017068571 A1 | 4/2017 |
| WO | 2017203251 A1 | 11/2017 |

OTHER PUBLICATIONS

International Search Report and Written Opinion dated Oct. 10, 2018 for International application No. PCT/US2018/043061.
International Search Report and Written Opinion dated Oct. 10, 2018 for International application No. PCT/US2018/043062.
Axel Schäfer et al: "Estimation of Breathing Rate from Respiratory Sinus Arrhythmia: Comparison of Various Methods", Annals of Biomedical Engnieering, Kluwer Academic Publishers-Plenum Publishers, NE, vol. 36, No. 3, Jan. 11, 2008 (Jan. 11, 2008), pp. 476-485, XP019568785, ISSN: 1573-9686, pp. 476-480.
Richard Singhathip et al: "Extracting Respiration Rate From Raw ECG Signals", Biomedical Engineering: Applications, Basis and Communications=Yixue-Gongc, World Scientific, TW, vol. 22, No. 4, Aug. 1, 2010 (Aug. 1, 2010), pp. 307-314, XP008169483, ISSN : 1016-2372, DOI: 10.4015/S1016237210002079 pp. 307-309.
Kim J M et al: "Two Algorithms for Detecting Respiratory Rate from ECG Signal", Imaging the Future Medicine : World Congress on Medical Physics and Biomedical Engineering 2006, Aug. 27-Sep. 1, 2006, Coex Seoul, K; [IFMBE Proceedings, vol. 14], Springer, DE, vol. 14, Jan. 1, 2007 (Jan. 1, 2007), pp. 4069-4071, XP008169469, DOI: 10 .1007/978-3-540-36841-0 1030 ISBN : 978-3-540-36839-7—the whole document.
International Search Report and Written Opinion dated Apr. 26, 2019 for PCT/US2019/014772.
International Search Report and Written Opinion dated Jul. 3, 2019 for PCT/US2019/014066.
Invitation to Pay Additional Fees and Partial International Search Report dated May 2, 2019 for PCT/US2019/014066.

* cited by examiner

EARPHONES FOR MEASURING AND ENTRAINING RESPIRATION

RELATED APPLICATIONS

This application is related to, and incorporates by reference, U.S. patent application Ser. No. 15/106,989, filed Jun. 21, 2016; application Ser. No. 15/348,400, filed Nov. 10, 2016; and application Ser. No. 15/352,034, filed Nov. 17, 2016, all titled Intelligent Earplug System. It is also related to U.S. patent application Ser. No. 15/267,567, entitled Sleep Assistance Device; application Ser. No. 15/267,464, entitled Sleep Quality Scoring and Improvement; application Ser. No. 15/267,552, entitled Intelligent Wake-Up System; application Ser. No. 15/267,848, entitled Sleep System; application Ser. No. 15/267,858, entitled User Interface for a Sleep System; and application Ser. No. 15/267,886, entitled Sleep Assessment Using a Home Sleep System, all of which were filed on Sep. 16, 2016. It is also related to U.S. patent application Ser. No. 15/655,836, filed Jul. 20, 2017, titled Sleep Assistance Device For Multiple Users, filed simultaneously with this application, which is incorporated here by reference.

BACKGROUND

This disclosure relates to earphones for measuring and entraining respiration.

Sleeplessness and poor or interrupted sleep may significantly affect a person's health. Poor sleep may be caused by such factors as ambient noise, stress, medical conditions, or discomfort. Thus, there exists a need for a sleep aid that can help address the underlying causes of poor sleep without adversely affecting the user's health in other, unintended ways.

SUMMARY

In general, in one aspect, a system includes an earphone including a loudspeaker, a microphone, a housing supporting the loudspeaker and microphone, and an ear tip surrounding the housing and configured to acoustically couple both the loudspeaker and the microphone to an ear canal of a user, and to acoustically close the entrance to the user's ear canal. A processor provides output audio signals to the loudspeaker which represent sounds across a first frequency band, the audio signals including a notch in which the sounds lack energy within a second frequency band narrower than the first frequency band, receives input audio signals from the microphone, applies a band-pass filter to the input audio signals to limit the input audio signals to a third frequency band contained within the second frequency band, and demodulates the filtered input audio signals to compute a rate of respiration corresponding to energy in the input audio signals in the third frequency band.

Implementations may include one or more of the following, in any combination. The third frequency band may be coextensive with the second frequency band. The first frequency band may extend at least 40 Hz below a lower end of the second frequency band. The second frequency band may extend between about 250 to 350 Hz. The processor may adjust the output audio signals based on the detected rate of respiration, and provide the adjusted output audio signals to the loudspeaker. Adjusting the output audio signals may include adjusting a rhythm of the output audio signals to be about one cycle per minute less than the detected respiration rate. Adjusting the output audio signals may include transitioning the output audio signals from respiration entrainment sounds to masking sounds. Adjusting the output audio signals may include transitioning the output audio signals from masking sounds to awakening sounds. The earphone may include a memory storing sound files, and providing the output audio signals may include retrieving a first sound file from the memory. The first sound file may represent audio signals corresponding to sounds having energy in the second frequency band, and providing the output audio signals may include applying a notch filter to audio signals generated from the first sound file, to remove energy from the signals within the second frequency band. The first sound file may represent audio signals corresponding to sounds lacking energy in the second frequency band. The processor may adjust the output audio signals based on the detected rate of respiration by retrieving a second sound file from the memory and using the second sound file to generate the output audio signal. The processor may be integrated within the earphone. The processor may be integrated within a portable computing device.

In general, in one aspect, measuring the respiration rate of a user of an earphone, includes receiving input audio signals from a microphone supported by a housing and acoustically coupled to the user's ear canal by an ear tip surrounding the housing and acoustically closing the entrance to the user's ear canal, and providing, to a loudspeaker in the housing and also acoustically coupled to the user's ear canal by the ear tip, output audio signals which represent sounds across a first frequency band, the audio signals including a notch in which the sounds lack energy within a second frequency band narrower than the first frequency band, and in a processor, applying a band-pass filter to the input audio signals to limit the input audio signals to a third frequency band contained within the second frequency band, and demodulating the filtered input audio signals to compute a rate of respiration corresponding to energy in the input audio signals in the third frequency band.

Advantages include acoustically sensing the respiration rate at the ear without interference from audio signals being generated by the earphone.

All examples and features mentioned above can be combined in any technically possible way. Other features and advantages will be apparent from the description and the claims.

DESCRIPTION

Several of the above-referenced applications describe a bedside system that detects a user's respiration rate and uses that to infer and manage their sleep state. In particular, to assist the user with falling to sleep, the system plays sounds that have a rhythm slightly slower than the user's own respiration rate. This naturally leads the user to slow their breathing to match the rhythm of the sounds, in a process referred to as entrainment. As the user slows their rate of respiration, the rate of the sounds is further reduced, in a feedback loop that leads the user gradually to sleep. Once the user falls asleep (as indicated by artifacts in their respiration rate), the system switches to playing masking sounds, which diminish the user's ability to detect, and be disturbed by, external sounds. If the user is detected to be waking up too early, entrainment may be reactivated. When it is time for the user to wake up, the system may coordinate wake-up sounds with the user's sleep state and other information to wake the user in the least-disruptive way possible.

Others of the above-referenced applications describe intelligent earplugs which the user can wear while sleeping, and which provide masking sounds through the night, and alarm or alert sounds when needed. These earplugs are controlled by a smartphone, but principally operate autonomously, playing stored masking sounds until instructed otherwise by the controlling phone, or based on an internal clock. It would be advantageous if the intelligent earplugs could play the respiration-entraining sounds of the bedside systems, to help the user fall asleep without disturbing others who may be sharing the bed or room. One solution to that, described in co-pending application Ser. No. 15/655,836, is for the sleep system to inform the earplugs of the user's respiration rate and sleep state, and for the earplugs to adjust the rate of a rhythmic component in stored entrainment sounds as in the out-loud system.

This disclosure describes how to add respiration sensing to the earplugs themselves, so that the external system is not required, and the earplugs can operate fully autonomously, or with only a smart phone to control them.

Figure 1:
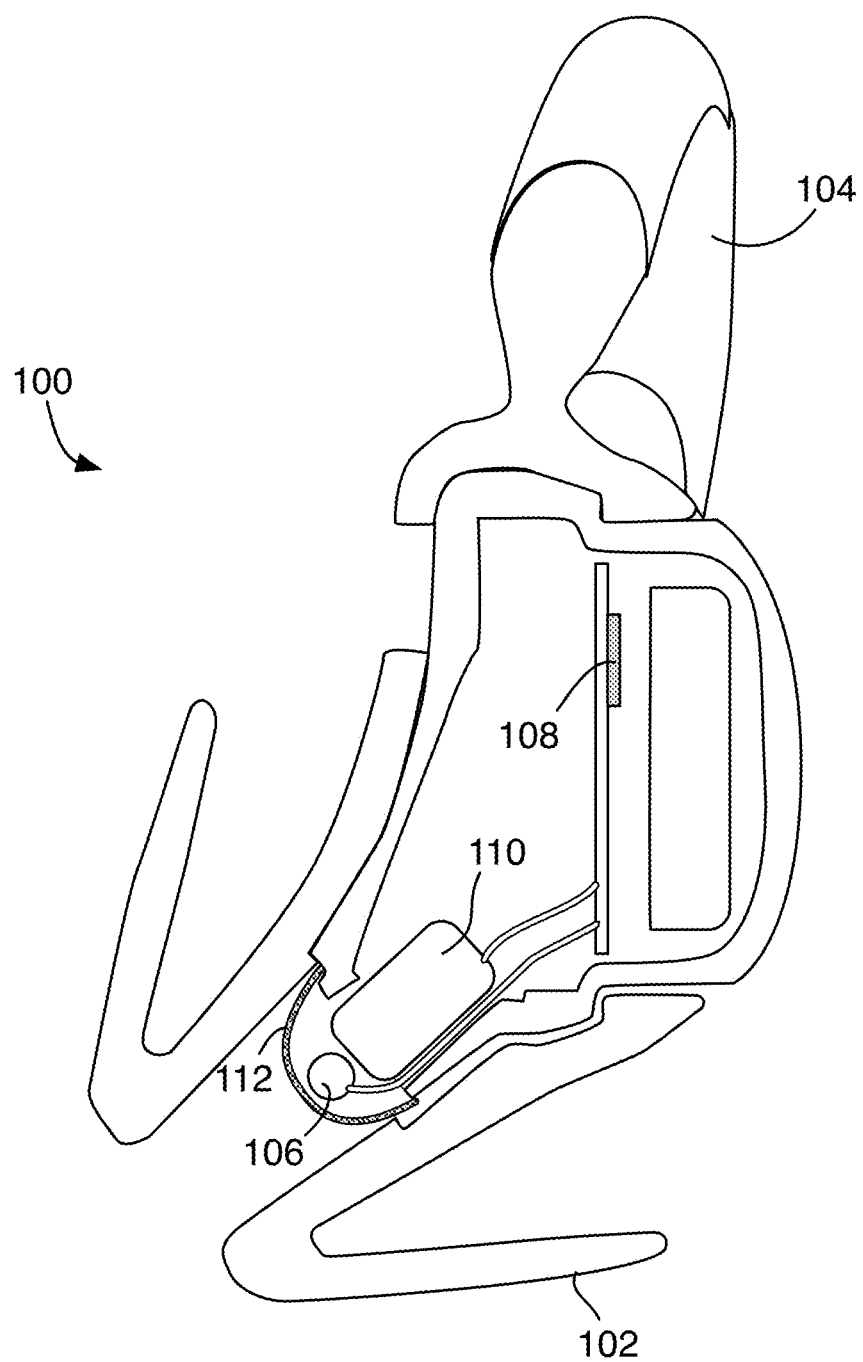
FIGS. 1 and 2 show cross-sectional views of earphones with an integrated microphones.
Figure 2:
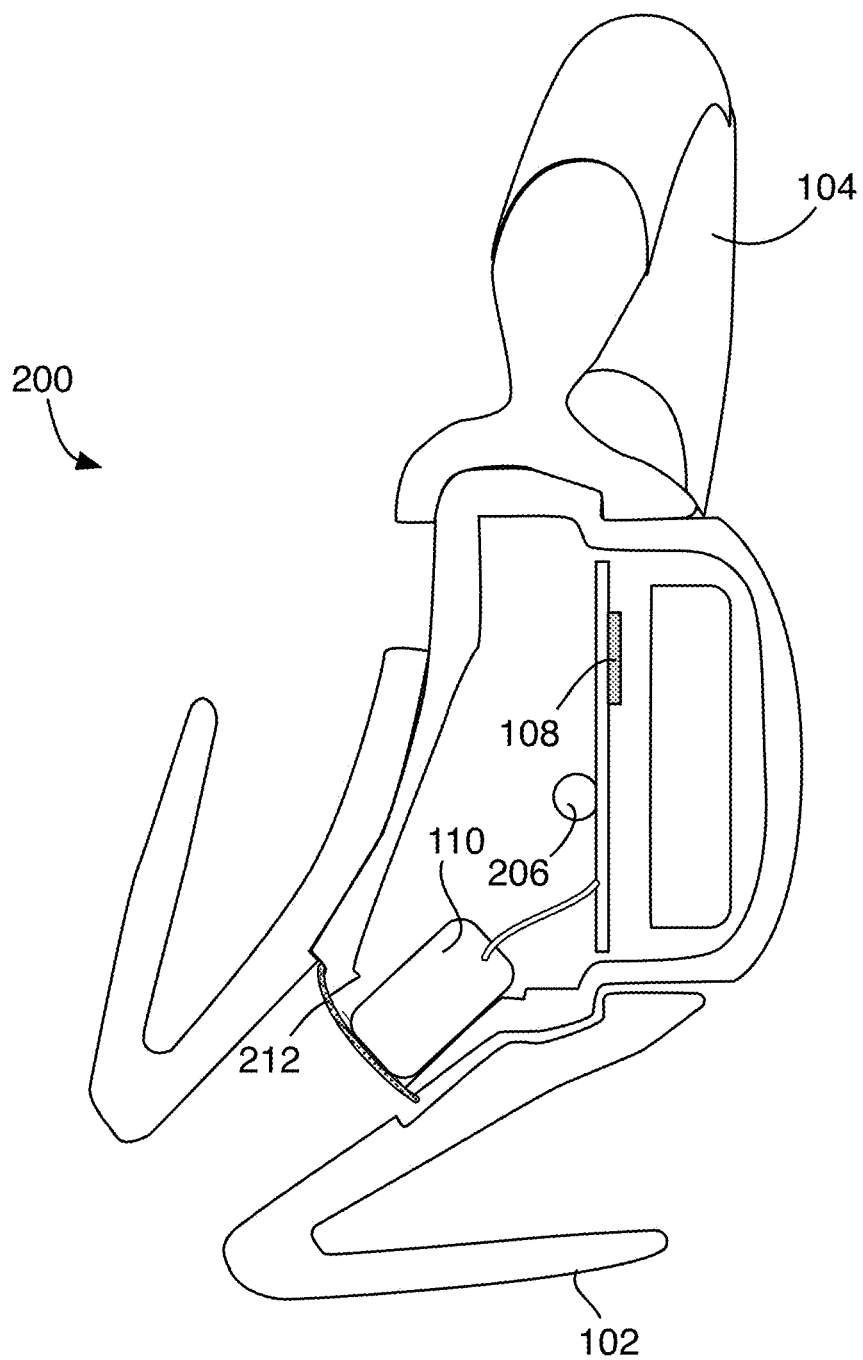
Figure 3:
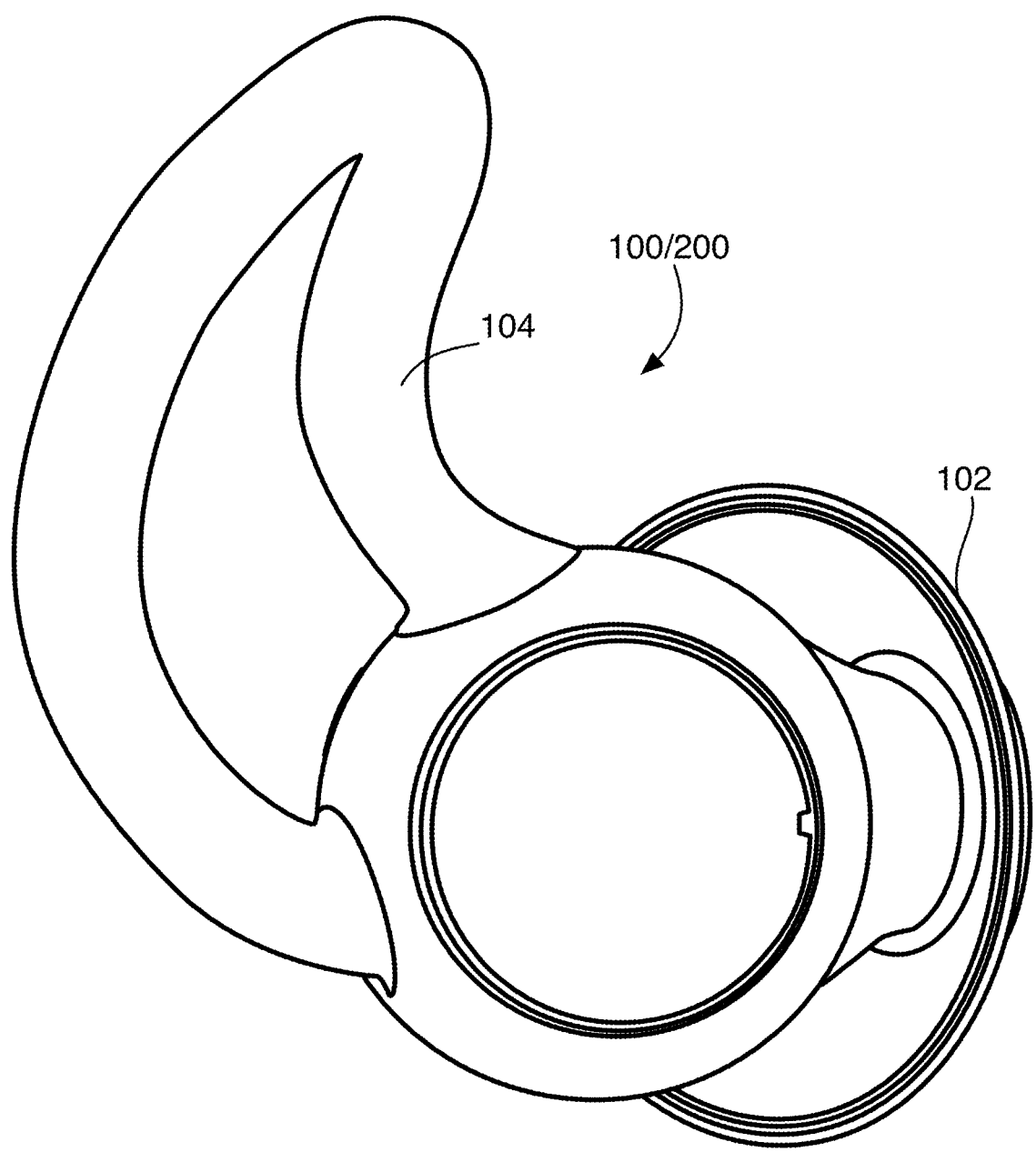
FIG. 3 shows an external view of The system of FIG. 1 or 2.

As shown in FIGS. 1, 2 and 3, sleep-sensing earphones 100 or 200 include an ear tip sealing structure 102 that blocks, or occludes, the entrance to the ear canal. FIGS. 1 and 2 show cross-sections of two different earphone examples, while FIG. 2 shows an exterior view, which is the same for the examples of either FIG. 1 or 2, for reference. A retaining structure 104 helps retain the earphone in the ear, and puts pressure on the sealing structure 102 to maintain the seal by pushing on the concha, opposite to where the sealing structure meets the ear canal. The sealing structure 102 helps to passively block outside sounds from entering the ear, increasing the effectiveness of the masking sounds played by the earphones.

Another result of occluding the ear canal is that sounds produced by the body, such as the heartbeat and respiration sounds, are amplified within the ear canal. With the addition of a microphone 106 (FIG. 1) or 206 (FIG. 2), the respiration can be sensed and its rate determined. The processor 108 on-board each earphone (or in one, if they coordinate their action) can then adjust the timing of entrainment sounds being played to the user through a speaker 110. In the example of FIG. 1, the microphone 106 and speaker 110 are shown behind a screen 112, as described in U.S. Pat. No. 9,635,452, which is incorporated here by reference. The microphone may be mounted near or on the speaker 110, or integrated into the speaker housing. In the example of FIG. 2, the microphone 206 is mounted directly to the PCB 208 and the screen 112 is flat, or may not be needed; the volume inside the earbud is coupled to the ear canal via space around the driver 110. As long as the earbud/ear canal system is effectively sealed at the frequencies of interest, the microphone will detect the targeted sounds coming from inside the ear canal. Other configurations that couple the microphone acoustically to the ear canal will also work.

Figure 4:
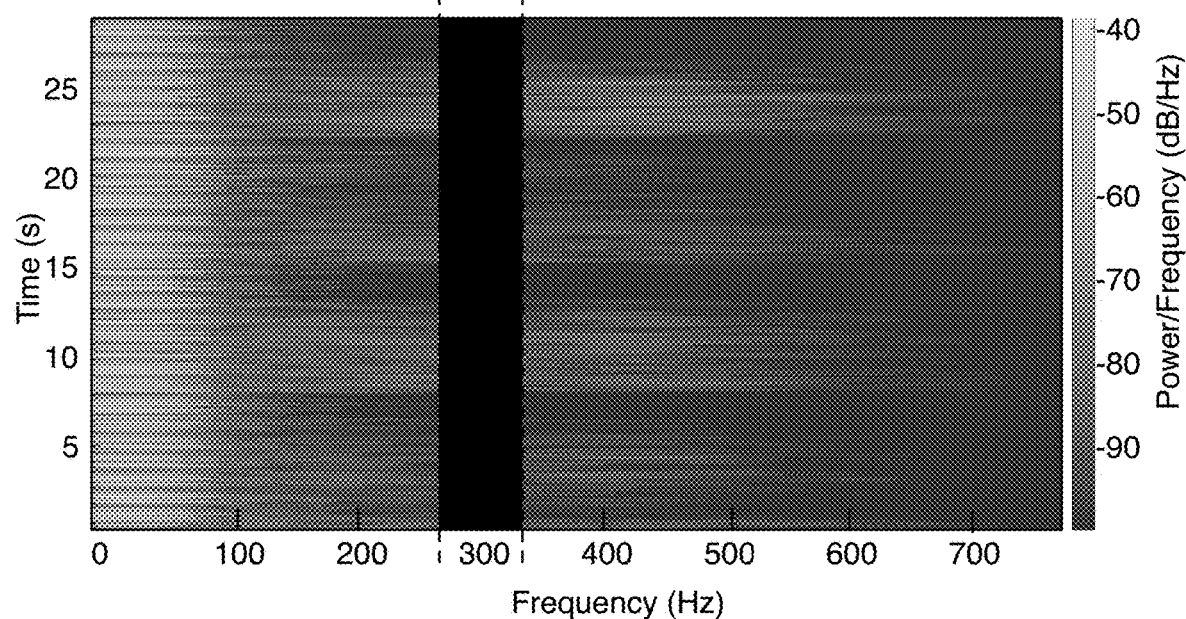
FIGS. 4, 5a, 5b, and 5c show audio spectrographs.
Figure 5A:
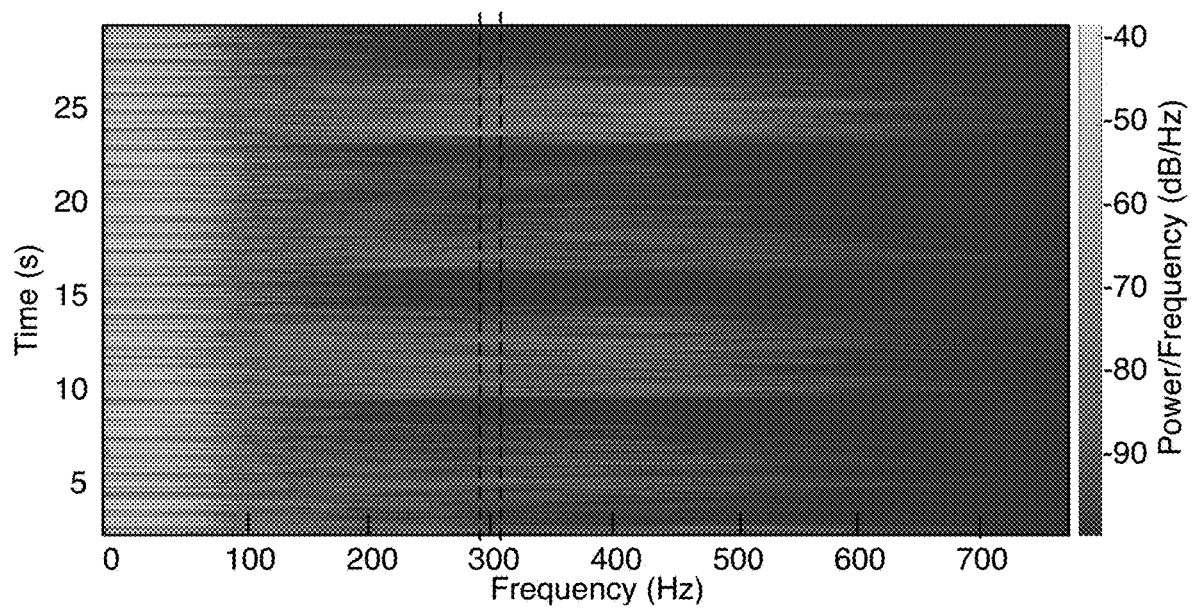
Figure 5B:
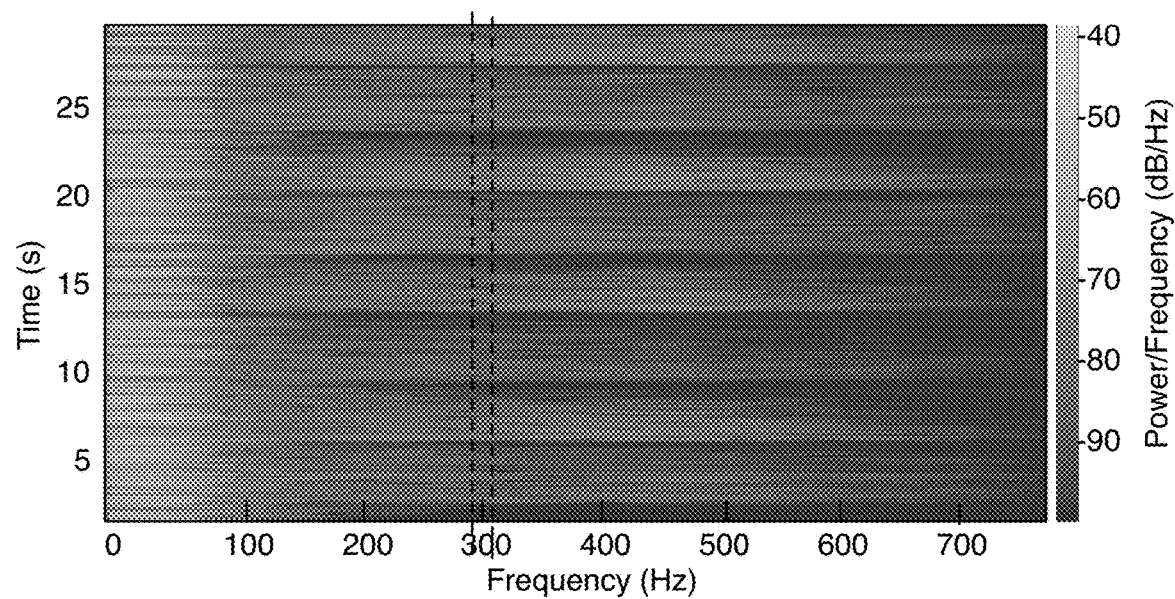
Figure 5C:
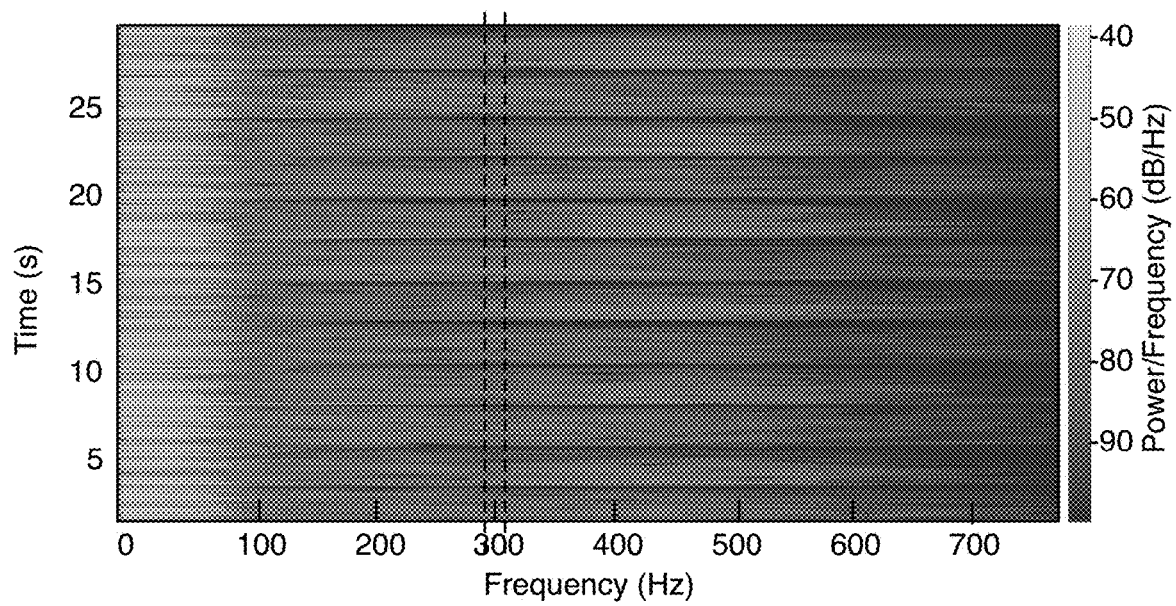

A difficulty arises in attempting to use a microphone coupled to the ear canal to detect respiration while the earphones are simultaneously playing sounds (and in particular, sounds which may not be significantly different from the sound of breathing). One solution, as shown in FIG. 4, is to notch out a small frequency band of the entrainment or masking sound, and to filter the microphone signal, shown in FIGS. 5a-5c for different respiration rates, with a corresponding band-pass filter. Due to the psychoacoustic phenomenon known as the upward spread of frequency, a user will not be able to audibly detect the small notch in the entrainment or masking sound, but enough of the sound of their respiration will be detectible within the notched and filtered window to measure their respiration rate.

Figure 6:
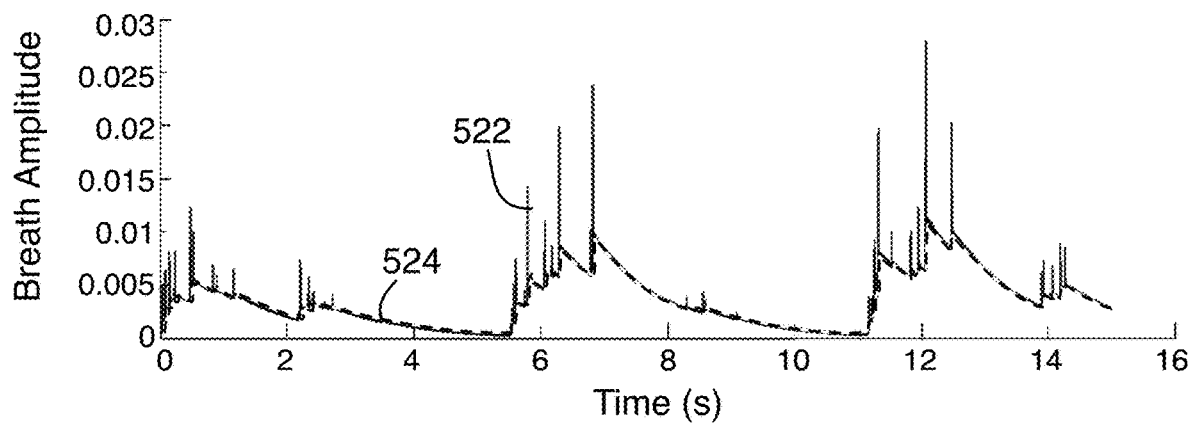
FIGS. 6 and 7 show graphs of data derived from the type of data shown in FIGS. 5a-5c.
Figure 7:
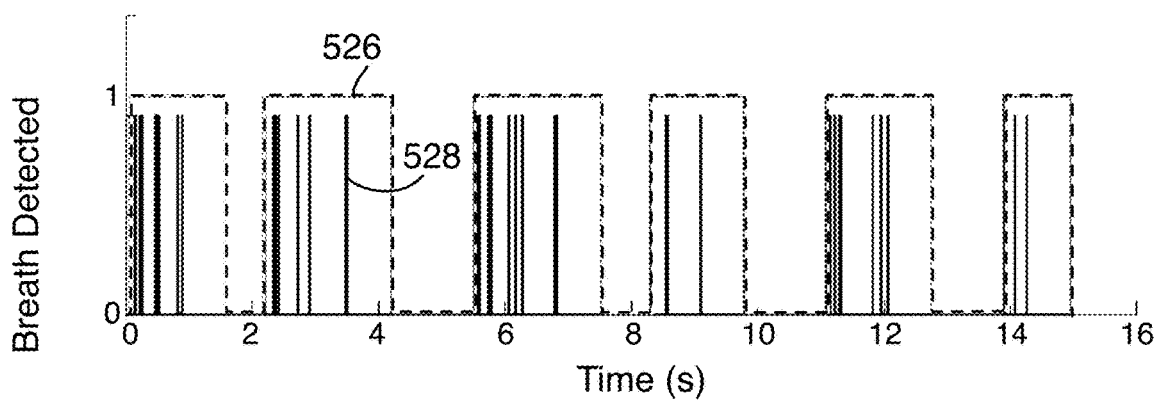

In particular, a notch in a range around 250-350 Hz will leave enough energy below the notch for the upper spread of frequency to hide the notch from the user. More specifically, a notch between 260-340 Hz has been found to be sufficient. The notch can either be removed from the masking or entrainment sound by a DSP during operation of the earplugs, or the stored sounds can simply have the notch already present. A band-pass filter matching, or narrower than, the notch band is then applied to the microphone signal (dashed lines 502, 504 in FIGS. 5a-5c), which can be visualized as energy over time, as shown by the solid line 522 in FIG. 6. The respiration envelope is fit to the data, dashed line 524. A peak detection algorithm is applied, as shown in FIG. 7, to detect the respiration of the user, the rate of the clusters 526 of peaks 528 corresponding to breaths per minute.

The human heartbeat is infrasonic, while acoustic signatures from respiration can be observed in the 100s of Hz, so the heartbeat will be too low-frequency (and the high-frequency part of the heart beat impulse too low-energy) to interfere with detection of respiration in the notched band. The heart beat could also be removed from the microphone signal using an additional heart rate sensor, such as a photo-plethysmograph (PPG) sensor included in the earphones.

If the earphones happen to include a feedback-based active noise reduction (ANR) system, to further block environmental sounds, the system microphone of the ANR system would be more than adequate for detecting the sound of respiration blood flow and computing its rate, but it would be done within the feedback loop, so notching the anti-noise output of the ANR system in the same manner as the entrainment or masking sounds would not be necessary. However, an ANR system is likely to consume a lot of power, and may not be suitable or necessary for sleep-focused earphones. Since the respiration or heart rate sensing is very narrow-band, a simpler MEMS microphone should be sufficient, and a much lower-power component may be used, benefiting the overall battery life and component size of the earphones. Similarly, it may be possible to use an external device, such as a smartphone, to filter and demodulate the microphone signals to detect the respiration rate or heart rate, and to modify the output sounds accordingly, but battery life may be better served by doing all the processing within the earphones. The trade-off between power for processing and power for communication may depend on factors unrelated to the acoustics, including battery size, antenna placement, and memory requirements, to name a few.

Embodiments of the systems and methods described above comprise computer components and computer-implemented steps that will be apparent to those skilled in the art. For example, it should be understood by one of skill in the art that the computer-implemented steps may be stored as computer-executable instructions on a computer-readable medium such as, for example, hard disks, optical disks, solid-state disks, flash ROMS, nonvolatile ROM, and RAM. Furthermore, it should be understood by one of skill in the art that the computer-executable instructions may be executed on a variety of processors such as, for example, microprocessors, digital signal processors, and gate arrays. For ease of exposition, not every step or element of the systems and methods described above is described herein as part of a computer system, but those skilled in the art will recognize that each step or element may have a corresponding computer system or software component. Such computer system and software components are therefore enabled by describing their corresponding steps or elements (that is, their functionality), and are within the scope of the disclosure.

A number of implementations have been described. Nevertheless, it will be understood that additional modifications may be made without departing from the scope of the inventive concepts described herein, and, accordingly, other embodiments are within the scope of the following claims.

What is claimed is:

1. A system comprising:
an earphone comprising:
a loudspeaker;
a microphone;
a housing supporting the loudspeaker and microphone;
an ear tip surrounding the housing and configured to acoustically couple both the loudspeaker and the microphone to an ear canal of a user, and to acoustically close the entrance to the user's ear canal; and
a processor configured to:
provide output audio signals to the loudspeaker which represent sounds across a first frequency band, the audio signals including a notch in which the sounds lack energy within a second frequency band narrower than the first frequency band;
receive input audio signals from the microphone;
apply a band-pass filter to the input audio signals to limit the input audio signals to a third frequency band contained within the second frequency band; and
demodulate the filtered input audio signals to compute a rate of respiration corresponding to energy in the input audio signals in the third frequency band,
wherein the first frequency band extends at least 40 Hz below a lower end of the second frequency band.

2. The system of claim 1, wherein the third frequency band is coextensive with the second frequency band.

3. A system comprising:
an earphone comprising:
a loudspeaker;
a microphone;
a housing supporting the loudspeaker and microphone;
an ear tip surrounding the housing and configured to acoustically couple both the loudspeaker and the microphone to an ear canal of a user, and to acoustically close the entrance to the user's ear canal; and
a processor configured to:
provide output audio signals to the loudspeaker which represent sounds across a first frequency band, the audio signals including a notch in which the sounds lack energy within a second frequency band narrower than the first frequency band;
receive input audio signals from the microphone;
apply a band-pass filter to the input audio signals to limit the input audio signals to a third frequency band contained within the second frequency band; and
demodulate the filtered input audio signals to compute a rate of respiration corresponding to energy in the input audio signals in the third frequency band,
wherein the second frequency band extends between about 250 to 350 Hz.

4. A system comprising:
an earphone comprising:
a loudspeaker;
a microphone;
a housing supporting the loudspeaker and microphone;
an ear tip surrounding the housing and configured to acoustically couple both the loudspeaker and the microphone to an ear canal of a user, and to acoustically close the entrance to the user's ear canal; and
a processor configured to:
provide output audio signals to the loudspeaker which represent sounds across a first frequency band, the audio signals including a notch in which the sounds lack energy within a second frequency band narrower than the first frequency band;
receive input audio signals from the microphone;
apply a band-pass filter to the input audio signals to limit the input audio signals to a third frequency band contained within the second frequency band; and
demodulate the filtered input audio signals to compute a rate of respiration corresponding to energy in the input audio signals in the third frequency band,
wherein the processor is further configured to adjust the output audio signals based on the detected rate of respiration, and provide the adjusted output audio signals to the loudspeaker,
wherein
the earphone further includes a memory storing sound files; and
providing the output audio signals comprises retrieving a first sound file from the memory, and
wherein:
the first sound file represents audio signals corresponding to sounds having energy in the second frequency band, and
providing the output audio signals further comprises, in the processor, applying a notch filter to audio signals generated from the first sound file, to remove energy from the signals within the second frequency band.

5. A system comprising:
an earphone comprising:
a loudspeaker;
a microphone;
a housing supporting the loudspeaker and microphone;
an ear tip surrounding the housing and configured to acoustically couple both the loudspeaker and the microphone to an ear canal of a user, and to acoustically close the entrance to the user's ear canal; and
a processor configured to:
provide output audio signals to the loudspeaker which represent sounds across a first frequency band, the audio signals including a notch in which the sounds lack energy within a second frequency band narrower than the first frequency band;
receive input audio signals from the microphone;
apply a band-pass filter to the input audio signals to limit the input audio signals to a third frequency band contained within the second frequency band; and demodulate the filtered input audio signals to compute a rate of respiration corresponding to energy in the input audio signals in the third frequency band, wherein the processor is further configured to adjust the output audio signals based on the detected rate of respiration, and provide the adjusted output audio signals to the loudspeaker, wherein the earphone further includes a memory storing sound files and providing the output audio signals comprises retrieving a first sound file from the memory, and wherein the first sound file represents audio signals corresponding to sounds lacking energy in the second frequency band.

6. A system comprising:
an earphone comprising:
a loudspeaker;
a microphone;
a housing supporting the loudspeaker and microphone;
an ear tip surrounding the housing and configured to acoustically couple both the loudspeaker and the microphone to an ear canal of a user, and to acoustically close the entrance to the user's ear canal; and
a processor configured to:
provide output audio signals to the loudspeaker which represent sounds across a first frequency band, the audio signals including a notch in which the sounds lack energy within a second frequency band narrower than the first frequency band;
receive input audio signals from the microphone;
apply a band-pass filter to the input audio signals to limit the input audio signals to a third frequency band contained within the second frequency band; and
demodulate the filtered input audio signals to compute a rate of respiration corresponding to energy in the input audio signals in the third frequency band, wherein the processor is further configured to adjust the output audio signals based on the detected rate of respiration, and provide the adjusted output audio signals to the loudspeaker, wherein the earphone further includes a memory storing sound files and providing the output audio signals comprises retrieving a first sound file from the memory, and wherein the processor is further configured to adjust the output audio signals based on the detected rate of respiration by retrieving a second sound file from the memory and using the second sound file to generate the output audio signal.

7. The system of claim 1, wherein the processor is integrated within the earphone.

8. The system of claim 1, wherein the processor is integrated within a portable computing device.

9. A method of measuring the respiration rate of a user of an earphone, the method comprising:
receiving input audio signals from a microphone supported by a housing and acoustically coupled to the user's ear canal by an ear tip surrounding the housing and acoustically closing the entrance to the user's ear canal; and
providing, to a loudspeaker in the housing and also acoustically coupled to the user's ear canal by the ear tip, output audio signals which represent sounds across a first frequency band, the audio signals including a notch in which the sounds lack energy within a second frequency band narrower than the first frequency band; and
in a processor,
applying a band-pass filter to the input audio signals to limit the input audio signals to a third frequency band contained within the second frequency band; and
demodulating the filtered input audio signals to compute a rate of respiration corresponding to energy in the input audio signals in the third frequency band,
wherein the first frequency band extends at least 40 Hz below a lower end of the second frequency band.

10. The method of claim 9, wherein the third frequency band is coextensive with the second frequency band.

11. A method of measuring the respiration rate of a user of an earphone, the method comprising:
receiving input audio signals from a microphone supported by a housing and acoustically coupled to the user's ear canal by an ear tip surrounding the housing and acoustically closing the entrance to the user's ear canal; and
providing, to a loudspeaker in the housing and also acoustically coupled to the user's ear canal by the ear tip, output audio signals which represent sounds across a first frequency band, the audio signals including a notch in which the sounds lack energy within a second frequency band narrower than the first frequency band; and
in a processor,
applying a band-pass filter to the input audio signals to limit the input audio signals to a third frequency band contained within the second frequency band; and
demodulating the filtered input audio signals to compute a rate of respiration corresponding to energy in the input audio signals in the third frequency band,
wherein the second frequency band extends between about 250 to 350 Hz.

12. A method of measuring the respiration rate of a user of an earphone, the method comprising:
receiving input audio signals from a microphone supported by a housing and acoustically coupled to the user's ear canal by an ear tip surrounding the housing and acoustically closing the entrance to the user's ear canal; and
providing, to a loudspeaker in the housing and also acoustically coupled to the user's ear canal by the ear tip, output audio signals which represent sounds across a first frequency band, the audio signals including a notch in which the sounds lack energy within a second frequency band narrower than the first frequency band; and
in a processor,
applying a band-pass filter to the input audio signals to limit the input audio signals to a third frequency band contained within the second frequency band; and
demodulating the filtered input audio signals to compute a rate of respiration corresponding to energy in the input audio signals in the third frequency band,
wherein the earphone further includes a memory storing sound files and providing the output audio signals comprises retrieving a first sound file from the memory, and
wherein:
the first sound file represents audio signals corresponding to sounds having energy in the second frequency band, and
providing the output audio signals further comprises, in the processor, applying a notch filter to audio signals generated from the first sound file, to remove energy from the signals within the second frequency band.

13. A method of measuring the respiration rate of a user of an earphone, the method comprising:

receiving input audio signals from a microphone supported by a housing and acoustically coupled to the user's ear canal by an ear tip surrounding the housing and acoustically closing the entrance to the user's ear canal; and providing, to a loudspeaker in the housing and also acoustically coupled to the user's ear canal by the ear tip, output audio signals which represent sounds across a first frequency band, the audio signals including a notch in which the sounds lack energy within a second frequency band narrower than the first frequency band; and in a processor, applying a band-pass filter to the input audio signals to limit the input audio signals to a third frequency band contained within the second frequency band; and demodulating the filtered input audio signals to compute a rate of respiration corresponding to energy in the input audio signals in the third frequency band, wherein the earphone further includes a memory storing sound files and providing the output audio signals comprises retrieving a first sound file from the memory, and wherein:

the first sound file represents audio signals corresponding to sounds lacking energy in the second frequency band.

14. A method of measuring the respiration rate of a user of an earphone, the method comprising:

receiving input audio signals from a microphone supported by a housing and acoustically coupled to the user's ear canal by an ear tip surrounding the housing and acoustically closing the entrance to the user's ear canal; and providing, to a loudspeaker in the housing and also acoustically coupled to the user's ear canal by the ear tip, output audio signals which represent sounds across a first frequency band, the audio signals including a notch in which the sounds lack energy within a second frequency band narrower than the first frequency band; and in a processor, applying a band-pass filter to the input audio signals to limit the input audio signals to a third frequency band contained within the second frequency band; and demodulating the filtered input audio signals to compute a rate of respiration corresponding to energy in the input audio signals in the third frequency band, wherein the earphone further includes a memory storing sound files and providing the output audio signals comprises retrieving a first sound file from the memory, and further comprising adjusting the output audio signals based on the detected rate of respiration by retrieving a second sound file from the memory and using the second sound file to generate the output audio signal.

* * * * *